United States Patent [19]
Brocia et al.

[11] Patent Number: 5,618,683
[45] Date of Patent: *Apr. 8, 1997

[54] DIAGNOSTIC KIT FOR CHOLESTERYL ESTER TRANSFER PROTEIN (CETP) ACTIVITY MEASUREMENT AND A NEW SYNTHETIC PARTICLE USED THEREIN

[76] Inventors: Robert W. Brocia, 15 Moore Rd., Bronxville, N.Y. 10708; Theresa L. Swenson, 445 E. 68th St., Apt. 8B, New York, N.Y. 10021

[*] Notice: The term of this patent shall not extend beyond the expiration date of Pat. No. 5,585,235.

[21] Appl. No.: 46,772

[22] Filed: Apr. 13, 1993

[51] Int. Cl.$^6$ .............................. C12Q 1/60; G01N 33/53
[52] U.S. Cl. .............................. 435/11; 435/7.92; 435/7.9; 435/4; 435/810; 435/975; 436/829; 436/809; 436/817; 514/2
[58] Field of Search .................................. 435/11, 7.92, 4, 435/7.9, 810, 975; 436/809, 829, 817; 514/2

[56] References Cited

U.S. PATENT DOCUMENTS

| | | | |
|---|---|---|---|
| 4,366,244 | 12/1982 | Pascal | 435/11 |
| 4,677,057 | 6/1987 | Curtiss et al. | 435/7.92 |
| 4,883,765 | 11/1989 | Tamic et al. | 435/11 |
| 4,892,815 | 1/1990 | Kerscher et al. | 435/11 |
| 5,118,613 | 6/1992 | Mc Gowan | 435/11 |
| 5,128,318 | 7/1992 | Levine et al. | 514/2 |
| 5,135,716 | 8/1992 | Thakore | 435/11 |
| 5,183,738 | 2/1993 | Adachi et al. | 435/11 |
| 5,217,873 | 6/1993 | Caris et al. | 435/11 |

OTHER PUBLICATIONS

Pattnaik et al, Biochimica et Biophysica Acta, 530 (1978) 428–438.
Dousset et al, Clinical Chem, vol. 38, No. 2, 1992.
Nichols et al, J. Lipid Research, vol. 6, pp. 206–210 (1965).
Milner et al, Biochimica et Biophysica Acta, 1082 (1991) 71–78.
Rye et al, J. of Lipid research, vol. 33, 1992, p. 215–224.
Craig et al, J. of Lipid research, vol. 22, 1981, pp. 687–696.
Effect of Very Low–Density Lipoproteins on Lipid Transfer in Incubated Serum, by A.V., Nichols and L. Smith, J. Lipid Research, vol. 6, pp. 206–210 (1965).
Cholesteryl Ester Exchange Protein in Human Plasma Isolation and Characterization by N.M. Pattnaik, A. Montes, L.B. Hughes and D.B. Zilversmit, Biochimica et Biophysica Acta 530, pp. 428–38 1978.
Fluorescent Determination of Cholesteryl Ester Transfer Protein (CETP) Activity in Plasma by N. Dousset, L. Douste-Blazy in Clinical Chemistry, vol. 38, No. 2, p. 306 (1982).
Enhanced of The Human Plasma Lipid Transfer Protein Reaction by Apolipoproteins by T.G. Milner, K.W.S. Ko, T. Ohnishi & S. Yokoyama in Biochimica Biophysica Acta 1082, pp. 71–78 (1991).

*Primary Examiner*—John Kight
*Assistant Examiner*—Louise N. Leary

[57] ABSTRACT

A diagnostic device is provided that determines the activity of CETP by the use of a new synthesized donor particle. The method in the diagnostic device for measuring the activity of cholesteryl ester transfer protein comprises: adding a prepared sonicated particle to a buffer to form a buffered solution, adding an Intralipid emulsion to the buffered solution for the purpose of accepting the transfer of neutral lipid, adding cholesteryl ester transfer protein to the buffered solution incubating the buffered solution, and reading the fluorescence of the buffer solution to measure the activity of the cholesteryl ester transfer protein. The synthesized donor particle is representative of a high density lipoprotein and comprises a fluorescent group, N-(7-nitrobenz-2-oxa-1,3-diazol-4-yl) amino-covalently bound to a cholesteryl ester to form a NBD-CE core, a monolayer of phospholipid that surrounds the NBD-CE core and an apolipoprotein apoA-I associated with the monolayer and an aqueous phase.

25 Claims, 2 Drawing Sheets

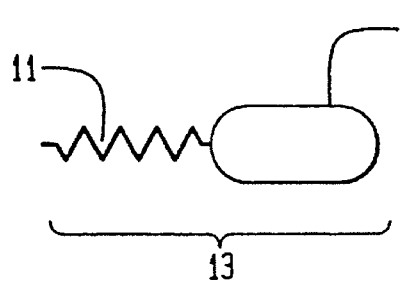
FIG. 1
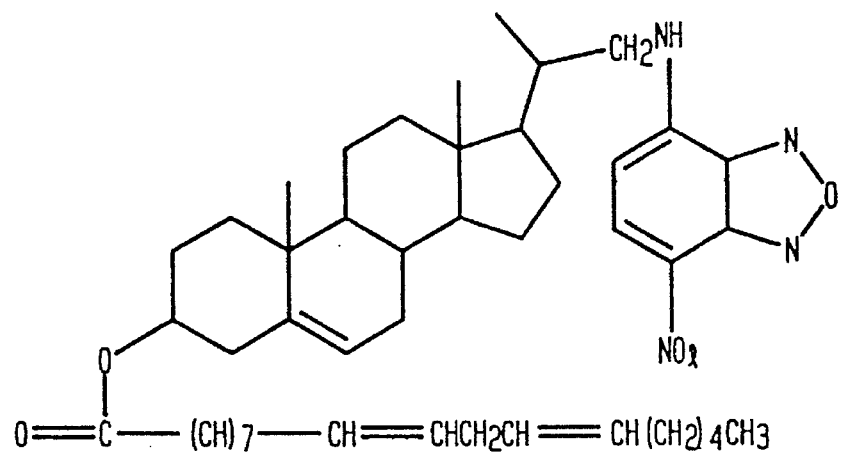
FIG. 2
FIG. 3
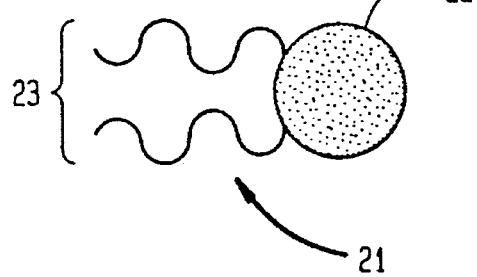

DIAGNOSTIC KIT FOR CHOLESTERYL ESTER TRANSFER PROTEIN (CETP) ACTIVITY MEASUREMENT AND A NEW SYNTHETIC PARTICLE USED THEREIN

BACKGROUND OF THE INVENTION

1. Field of the Invention

This invention relates to the field of medical diagnostic kits and a method for activity measurement of a protein. More particularly, it relates to a reagent device or kit that measures cholesteryl ester transfer protein (CETP) activity.

2. Description of the Prior Art

Cholesteryl ester transfer protein (CETP) is a protein that transfers cholesteryl ester (CE) from high-density lipoprotein (HDL) to low-density lipoprotein (LDL) and very-low density lipoprotein (VLDL). CETP will also transfer triglyceride (TG) among lipoprotein particles. For example, when a sample of VLDL or LDL, 1 or 10 micrograms of protein, respectively, is mixed with a sample of HDL, at total HDL cholesteryl ester of 4EE-10 moles, incubated at thirty seven degrees centigrade with a source of CETP, such as, one microliter of human plasma, cholesteryl ester will be transferred from the HDL to the LDL or VLDL particles. Typically, measurement of the CETP activity requires the cholesteryl ester associated with the HDL be provided with some type of label for monitoring the movement of the HDL cholesteryl ester to the LDL and VLDL components after incubation. The activity measurement techniques also usually require a final separation step after incubation so that either accumulation of HDL cholesteryl ester in LDL or VLDL may be quantified, or loss of HDL cholesteryl ester from HDL may be quantified. The HDL particle represents a donor of CE and the VLDL or LDL represent acceptors of CE.

There are several known techniques to measure cholesteryl ester transfer protein (CETP) activity. For example, an article entitled: Effect of Very Low-Density Lipoproteins on Lipid Transfer in Incubated Serum, by A. V. Nichols and L. Smith, J. Lipid Research, vol. 6, pp. 206–210 (1965), measures the activity of CETP by determination of cholesteryl ester (CE) mass transfer. The determination of CE mass transfer from high density lipoprotein (HDL) to very-low density lipoprotein (VLDL) and low density lipoprotein (LDL) requires the re-isolation of VLDL and LDL after incubation with HDL and the CETP source in order to determine the cholesteryl ester mass transfer.

The VLDL/LDL re-isolation from the incubation mixture is a technique that includes ultra-centrifugation of the incubation mixture for many hours so that the VLDL and LDL components are floated upwards through a density gradient as the HDL component of the incubation mixture sinks to the bottom of the centrifuge tube. Further processing of the sample requires a method of determining the amount or mass of cholesteryl ester associated with the re-isolated VLDL or LDL and equating a change in mass to CETP facilitated transfer. Later variations of this method of activity measurement have simplified mass determination by utilizing HDL that has a radioactive label associated with the CE.

While not stated in this article, the determination of CETP activity through tritium (3H) labeled cholesteryl ester (3H-CE) still requires the time consuming step of VLDL/LDL component re-isolation, or separation of VLDL or LDL from the 3H-CE containing HDL before the counts per minute of 3H-CE transferred can be determined. The present invention does not require the separation of any components of the incubation mixture nor does the present invention use radioactive isotopes.

An article entitled: Cholesteryl Ester Exchange Protein in Human Plasma Isolation and Characterization by N. M. Pattnaik, A. Montes, L. B. Hughes and D. B. Zilversmit, Biochimica et Biophysica Acta 530, pp. 428–438 (1978), discloses a method of activity measurement of CETP that also utilizes radioactive CE in HDL. This method is an improvement over the above method by simplifying the incubation mixture components separation or the re-isolation technique discussed above. In the cited article, separation of the LDL component from the HDL component is accomplished by precipitation of the LDL component of the incubation mixture. The LDL precipitate is pelleted by a relatively short, slow-speed centrifugation and the remaining HDL supernatant is counted. The loss of radioactivity from the HDL component is attributed to 3H-CE transferred to the LDL pellet. This method requires the use of radioactive isotopes and it is believed both prior art publications yield poor sensitivity and accuracy, characteristic of methods that require a high incident of sample manipulation.

An article titled: Fluorescent Determination of Cholesteryl Ester Transfer Protein (CETP) Activity in Plasma by N. Dousset and L. Douste-Blazy in Clinical Chemistry, vol. 38, No. 2, p. 306 (1982), is an improvement over previous methods of activity measurement since it discloses a technique that does not require radioactive components. In this method, transfer activity of the CETP is determined by the measurement of transfer of a fluorescent labeled CE. In this article, the cholesteryl ester molecule utilized as the CETP substrate for transfer, has been bonded to a fluorescent molecule derived from pyrene. The pyrene labeled cholesteryl ester (PY-CE) is recognized by the CETP and the PY-CE may be detected by a fluorimeter. The accumulation of the PY-CE in the LDL fraction is, however, only able to be determined after the separation of the LDL acceptor from the HDL donor.

An article entitled: Enhancement of The Human Plasma Lipid Transfer Protein Reaction by Apolipoproteins by T. G. Milner, K. W. S. Ko, T. Ohnishi and S. Yokoyama in Biochimica Biophysica Acta 1082, pp. 71–78 (1991), discloses a method for determining the activity of CETP also utilizing a pyrene labeled CE (PY-CE). This method does not require separation or re-isolation of substrates, but uses the measurement of both monomer and excimer fluorescent emission from the pyrene label to determine a ratio thereof. The cited article is improving upon certain aspects of the previous method. However, the method is based upon excimer to monomer ratio to determine accumulation of PY-CE in the acceptor and does not account for lipoprotein core viscosity changes affecting the excimer to monomer ratio. Pyrene labels have been used extensively in physical biochemistry to study particle core viscosity. This cited method results in problems with accuracy as noted in this article. The method is inconvenient due to oxygen quenching of excimer emission and requires the constant gassing of samples with nitrogen.

The present diagnostic kit is readily usable for the purpose of performing simple rapid and accurate tests to determine activity of CETP in a patient or group of patients. The kit does not utilize radioactive isotopes nor does the kit require the separation of donor and acceptor particles to accomplish activity measurements. The present kit yields a real time activity. Also, the reagent substrate emission is not subject to quenching by oxygen.

SUMMARY OF THE INVENTION

It is a principal object of this invention to provide a diagnostic device for rapid and accurate determination of CETP activity in a sample.

It is another object of the present invention to provide such a diagnostic device for individuals in the field for the purpose of determining the relative activity of CETP.

It is still another object of the present invention to provide such a diagnostic device that is accurate and without utilization of radioisotopes.

It is yet another object of the present invention such a diagnostic device that indicates to a physician if a child or adult has high CETP activity so the physician may recommend modification of the individual's diet before atherosclerosis is evidenced.

It is a further object of the present invention to provide a new synthetic donor particle that is used in such a device.

To the accomplishments of the foregoing objects and advantages, the present invention, in brief summary, comprises a diagnostic kit that determines the activity of CETP by the use of a newly synthesized donor particle.

The present invention also includes a method for measuring the activity of cholesteryl ester transfer protein, the method comprising the steps of: adding a prepared sonicated particle to a buffer to form a buffered solution simulating physiological conditions and adding an emulsion of lipid to the buffered solution of prepared sonicated particle. The lipid emulsion added is to act as an acceptor particle to accept CETP mediated transfer of NBD-CE. The acceptor lipid emulsion may be a commercially available preparation, such as that marketed under the trade name "Intralipid". A source of CETP is added to the buffered solution. The CETP source may be normal human plasma. The buffered mixture is incubated, and the fluorescence of the solution is read to measure the activity of cholesteryl ester transfer protein.

The synthesized donor particle of the present invention comprises: a NBD-CE core, a monolayer of PC that surrounds the NBD-CE core and human apolipoprotein A-I (apoA-I) dispersed within the monolayer. The donor particle is representative of a high density lipoprotein particle.

BRIEF DESCRIPTION OF THE DRAWINGS

The foregoing and still other objects and advantages of the present invention will be more apparent from the following detailed explanation of the preferred embodiments of the invention in connection with the accompanying drawings wherein:

FIG. 1 is an exploded diagrammatic representation of a fluorescent lipid component of the synthetic emulsion particle of the present invention;

FIG. 2 is the molecular structure of the synthetic emulsion particle of FIG. 1;

FIG. 3 is an exploded diagrammatic representation of the phospholipid emulsifier used in the present invention;

DESCRIPTION OF THE PREFERRED EMBODIMENTS

Cholesteryl ester transfer protein (CETP) is a protein that may be isolated from the plasma of normal humans. CETP substrates include two neutrally charged or non-polar lipids, namely cholesteryl esters (CE) and triglycerides (TG).

These neutral lipids are hydrophobic and present within the core of lipoprotein particles. They include, but are not limited to, high density lipoprotein (HDL), low density lipoprotein (LDL), intermediate density lipoprotein (IDL) and very low density lipoprotein (VLDL). Most lipoproteins are freely circulating in the plasma. The CETP transfers the two neutral lipids CE and TG from one lipoprotein particle, the donor, to another lipoprotein particle, the acceptor. A common donor-acceptor interaction is the transfer of the lipid CE from the lipoprotein HDL to the lipoprotein VLDL.

Referring to the figures and in particular, FIG. 1, in a preferred embodiment the present invention uses the fluorescent group, N-(7-nitrobenz-2-oxa-1,3-diazol-4-yl) amino-, referred to as NBD 11, covalently bonded to cholesteryl ester (CE) 12 to form the NBD-CE 13 shown in FIG. 2. The NBD-CE 13 is 22-(N-(7-nitrobenz-2-oxa-1,3-diazol-4-yl) amino)-23,24-bisnor-5-cholen-3B-yl linoleate (NBD-cholesteryl linoleate). CETP will transfer both cholesteryl esters and triglycerides which are both classified as neutral lipids because they are non-polar with respect to charge. The preferred method disclosed in the present invention will be valuable in the measurement of all neutral lipid transfer but will be discussed with respect to only CE transfer.

The NBD 11 labeled CE 12 forms a CE analogue NBD-CE 13. The NBD-CE 13 demonstrates a unique property associated with the fluorescent emission spectra. This property can be described as follows. If the NBD-CE 13 is contained in a highly concentrated area and is illuminated by a light of wavelength 465 nm, the fluorescent emission intensity will be less than that of the same NBD-CE in an area at a lower concentration. The NBD lipid or NBD-CE 13 illuminated by an excitation source and excited above the ground state will either fluoresce (unquenched) or lose the energy by means of radiationless transitions (quenched).

Figure 4:
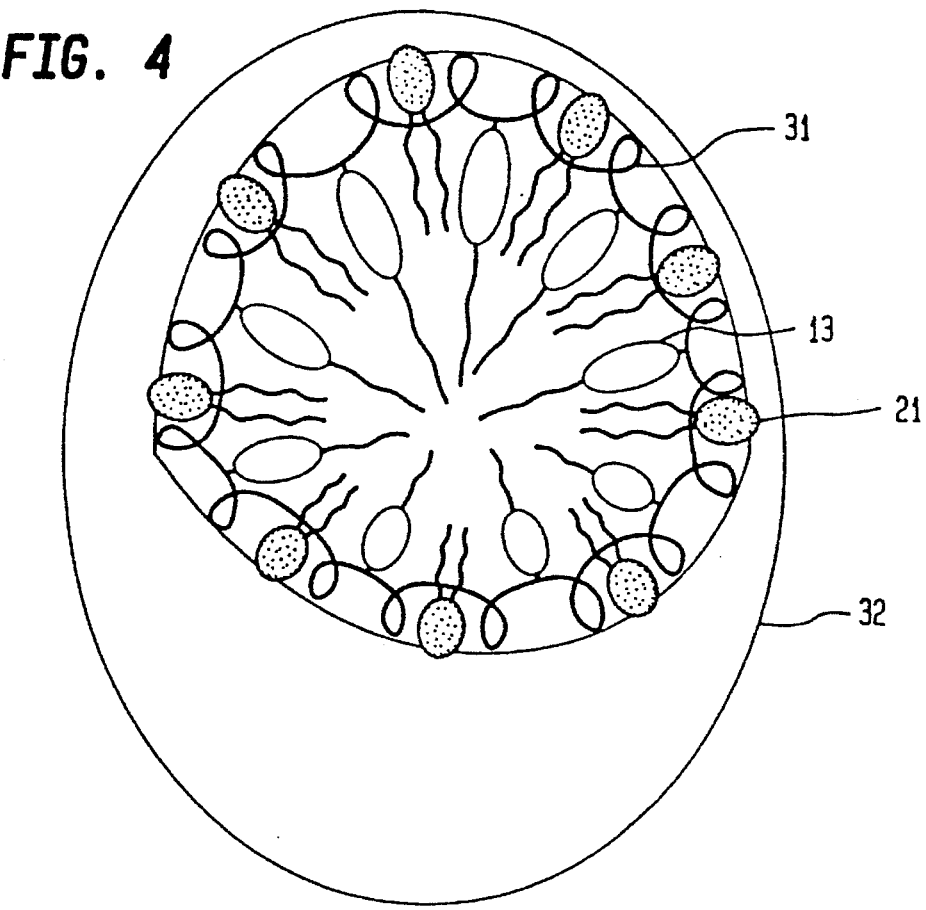
FIG. 4 is a cross section of the synthetic emulsion particle used in the present invention.

In a preferred embodiment of the invention, a self-quenching fluorescent neutral lipid, such as NBD-CE 13 of FIG. 1, is emulsified by a suitable emulsifier such as phospholipid, like phosphatidylcholine (PC) 21 of FIG. 3 to form a monolayer that surrounds the NBD-CE core 13 as shown in FIG. 4. Although the term emulsify is exemplified by a specific technique below, the present invention is concerned with incorporating the NBD lipid into an emulsified particle efficiently so as to achieve self-quenching emission characteristics of the label. There are many techniques known to emulsify a hydrophobic particle and many compounds that will act as emulsifying agents.

The emulsion is prepared by sonicating 2.8E-5 moles of N-(7-nitrobenz-2-oxa-1,3-diazol-4-yl) amino (NBD) labeled neutral lipid with 13 mg of phosphatidylcholine (PC) at a power output just under that which causes the sonic probe to cavitate within the sample. A temperature of 50 degrees centigrade is maintained for 45 minutes in a buffer 10 ml of 0.1M KCl/10 mM tris pH 8. The temperature is then lowered to 40 degrees centigrade and sonication energy to ⅔ of that which causes probe cavitation and 12 mg of an apoA-I protein (found in HDL) in 800 uL 2.5M urea is added over 15 minutes. The mixture is slow speed centrifuged to remove titanium.

Alternatively, the sonication temperature should initially (before the addition of apoA-I) be maintained within several degrees above or below the melting point (approximately 100 degrees centigrade) of the NBD-CE. The emulsification process of NBD-CE may be facilitated with the addition of a higher melting point phospholipid, such as dimyristoylphosphatidylcholine (DMPC), under these alternative conditions.

The synthetic emulsion is isolated from the crude sonication mixture by adjusting the sonication mixture to a density of 1.063 g/ml by the addition of solid sodium bromide (NaBr). A portion (2 ml) of the mixture is carefully overlaid into a 3 ml ultracentrifuge tube containing 0.2 ml of 1.4 g/ml sodium bromide solution. A saline solution (density=1.006 gm/ml, 0.2 ml) is layered on top of the crude sonication mixture. The tube containing the three density, overlaid solutions is centrifuged at 35,000 x g for ten (10) hours. To harvest the working NBD-CE emulsion from the centrifuged tube, 0.25 ml of the top layer is aspirated from the tube, the next volume of 1.9 ml is collected as the emulsion. Isolation of the synthetic emulsion by this method yields a particle of density less than 1.4 g/ml and greater than 1.006 g/ml. The non-emulsified NBD-CE will float to the top of the centrifuge tube while free or aggregated apoA-I will sink to the bottom.

FIG. 4 illustrates the PC/NBD-CE particle that results from the sonication, namely a NBD-CE core 13 surrounded by a monolayer of PC 21 with apoA-I 31 dispersed within the monolayer and associated with an aqueous phase that surrounds the particle. The particle 32 synthesized is representative of a high density lipoprotein (HDL) particle. The NBD-labeled neutral lipid NBD-CE 13 contained within the core of the synthetic particle will not yield a substantial fluorescent emission intensity when illuminated with excitation wavelength. Instead, the energy of the excited state is dissipated in radiationless energy transitions upon collision with other NBD-CE molecules. The non-fluorescent loss of energy is dependant upon molecular interactions associated with the core sequestered NBD-neutral lipid.

The monolayer of PC molecules 21 of FIG. 4, in the synthetic particle 32, is further illustrated in FIG. 3. PC is comprised of a polar head group 22, and non-polar or hydrophobic tail 23, the conditions under which the co-sonication is performed enables the non-polar or hydrophobic tail 23 of the PC molecule to partition with the hydrophobic NBD-neutral lipid, NBD-CE 13 of FIG. 1. The partitioning of hydrophobic constituents of the co-sonication mixture traps the NBD-neutral lipid into a small area relative to the area of the aqueous phase. The PC emulsified NBD-neutral lipid components are in a stable non-aqueous or hydrophobic environment at high concentration with respect to collisional proximity and accordingly yield little fluorescence intensity.

The diagnostic device or kit for CETP activity includes the addition of a suitable amount, such as 300 picomoles of synthetic NBD-labeled neutral lipid emulsion to a first container and adding 500 microliters of buffer. The preferred buffer includes 10 millimolars (mM) of trizma hydrochloride (HCl), 150 mM of sodium chloride (NaCl) and 2 mM of ethylenediaminetetraacetic acid (EDTA), all buffer to pH 7.4. A suitable amount of acceptor particle or emulsion, such as a commercially available preparation sold under the trade name "Intralipid" by KabiVitrum Inc. of Alameda, Calif., is then added to the buffered mixture in the first container for the purpose of accepting the transfer of neutral lipid. The acceptor will function as a sink for CETP mediated labeled neutral lipid transfer from the donor source. A suitable amount of CETP source is then added to the solution in the first container. A control for measurement purposes would be a second container made the same way as the first container, except that the CETP source is not added to the second container, and instead a volume of saline solution would be added as a control. The volume of saline solution is equivalent to the volume of the CETP source in the first container. In an alternative embodiment, both containers may contain plasma or other CETP source, yet one would be established as the control by incubating it at 4 degrees.

It should be understood that other lipid emulsions may be used, however Intralipid by KabiVitrum Inc. is presently preferred. This particular emulsion is a ten percent intravenous fat emulsion. Specifically, it includes 10 grams per one hundred milliliter (ml) of soybean oil, 1.2 grams/one hundred ml of phospholipids from powdered egg yoke, 2.25 grams/one hundred ml of glycerin and the remaining amount (q.s.) water.

Both containers are incubated at 37 degrees centigrade for a suitable amount of time and the fluorescence at 538 nanometers (nm) is read at an excitation wavelength of 465 nm in a standard laboratory fluorimeter. The first container, that received the human plasma or other CETP source, would be observed in the fluorimeter as increasing in florescence intensity over the incubation period. The second container, not receiving plasma but receiving a representative volume of saline solution, would not change in fluorescence intensity when measured in a fluorimeter. The background florescence would then be determined by the second container and the intensity value subtracted from that of the first container. This kit or method is independent of the proportions present of the prepared sonicated or synthetic particle, the acceptor emulsion and the CETP source. The method only requires the addition of the synthetic particle at an amount within the detection limit of the fluorimeter used for the measurement. The ratio of the acceptor emulsion or particles to the synthetic particles is kept high enough so that intra-particle transfer of NBD-CE between synthetic donor particles does not occur. Additionally, the diagnostic kit is formulated with standard proportions to allow activity measurements of CETP to be compared from laboratory to laboratory.

Figure 5:
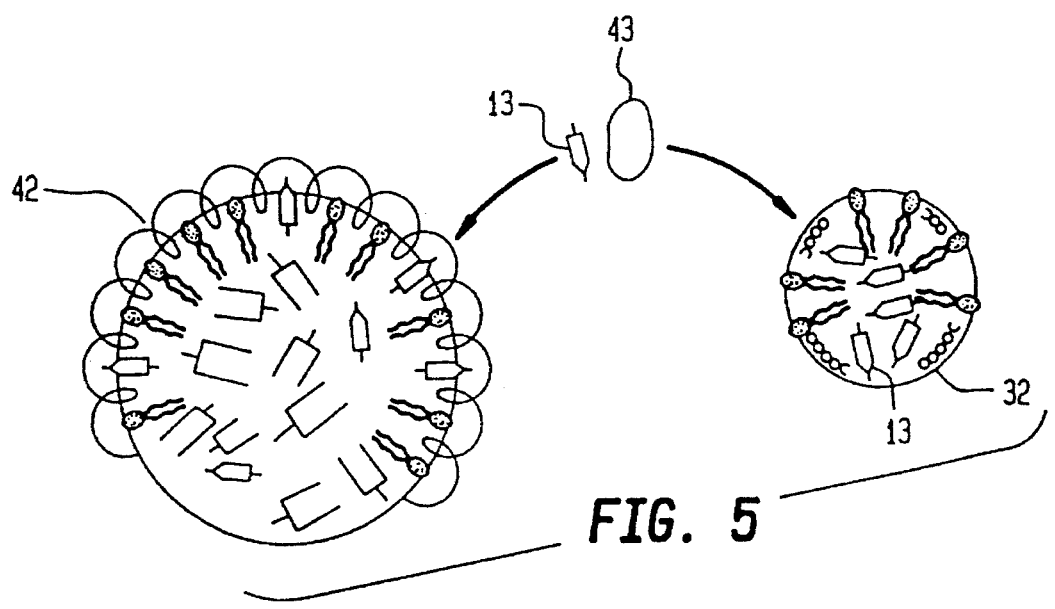
FIG. 5 illustrates a schematic of the transfer process measured by the device of the present invention.

FIG. 5 illustrates a schematic of the transfer process measured by the preferred kit or diagnostic device. The kit includes an amber colored glass vial with 10 milliliters (ml) of a liquid mixture that comprises 125 microliters of the prepared sonicated particle described in FIG. 4 and 9.875 milliliters (ml) of the buffer or solution of 10 millimolars of trizma hydrochloride (HCL), 150 millimolars of sodium chloride (NaCL) and 2 millimolars of ethylenediaminetetraacetic acid (EDTA) (tetrasodium salt hydrate). The buffer or solution is at a near physiological pH or pH of 7 to 8, preferably 7.4. The kit also includes a glass vial with a solution comprising 50 microliters of an acceptor, namely a lipid emulsion of triglyceride and phosphatidylcholine (10% triglyceride), such as that described above sold under the trade name "Intralipid" by KabiVitrum Inc., and 9.5 ml of a buffer or solution of 10 millimolars of HCL, 150 millimolars of NaCL and 2 millimolars of EDTA, also at a near physiological pH or pH of 7 to 8, preferably 7.4. To utilize the present invention, equal volumes of each vial are dispensed into a sample container. A volume of one four hundredth of the total volume of a patients plasma is added, and the mixture is allowed to incubate with the change in florescence intensity monitored according to the present invention.

As shown in FIG. 5, the transfer process includes the CETP 43 interacting with the prepared synthetic NBD-CE emulsion 32 and shuttles NBD-CE molecules 13 away from the core of the emulsion. The CETP 43 releases the NBD-CE 13 to an acceptor particle 42. The florescent intensity of the NBD-CE increases as the NBD-CE is moved from the synthetic HDL type sonicated emulsion 32 to the acceptor particle 42.

The diagnostic kit is a valuable tool. It can be used to screen a large population of patients to uncover those with genetic idiosyncrasies such as hyperalphalipoproteinemia, a disorder characterized by the absence of CETP in humans. It can also be used to screen for antibodies to CETP in a large number of samples, and to identify other inhibitors of CETP.

Having thus described the invention with particular reference to the preferred forms thereof, it will be obvious that various changes and modifications may be made therein without departing from the spirit and the scope of the invention as defined by the appended claims.

We claim:

1. A synthesized donor particle for donating a cholesterol ester or derivative thereof to a neutral lipid transfer protein comprising:

a fluorescent group covalently bonded to a cholesteryl ester to form a N-(7-nitrobenz-2-oxa-1,3-diazol-4-yl)amino-cholesteryl ester (NBD-CE) core;

a monolayer of phospholipid that surrounds the NBD-CE core; and an apolipoprotein apoA-I dispersed within the monolayer and associated with an aqueous phase that surrounds the particle and the monolayer.

2. The synthesized donor particle according to claim 1, wherein the fluorescent group is N-(7-nitrobenz-2-oxa-1,3-diazol-4-yl) amino.

3. The synthesized donor particle according to claim 1, wherein the monolayer is a phosphatidylcholine monolayer.

4. The synthesized donor particle according to claim 2, wherein the monolayer is a phosphatidylcholine monolayer, and wherein the donor particle represents a high density lipoprotein particle.

5. The synthesized donor particle according to claim 1, wherein the NBD-CE core is a fluorescent neutral lipid.

6. The synthesized donor particle according to claim 5, wherein the core will not yield a substantial fluorescent emission intensity when illuminated with an excitation wavelength.

7. A synthesized donor particle for donating a cholesterol ester or derivative thereof to a neutral lipid transfer protein comprising:

a fluorescent labeled core, N-(7-nitrobenz-2-oxa-1,3-diazol-4-yl) amino- covalently bonded to a cholesteryl ester to form a CE analogue NBD-CE, wherein the NBD-CE when contained in an area has a fluorescent emission intensity that is less in a highly concentrated area than in a lower concentration area;

a monolayer of phosphatidylcholine that surrounds the NBD-CE core; and an apolipoprotein apoA-I dispersed in the monolayer associated with an aqueous phase that surrounds the particle and the monolayer, wherein the donor particle represents a high density lipoprotein particle.

8. The synthesized donor particle according to claim 7, wherein the NBD-CE illuminated by an excitation source and excited above the ground state will either fluoresce or lose the energy by means of radiationless transitions.

9. A synthesized donor particle for donating a cholesterol ester or derivative thereof to a neutral lipid transfer protein comprising 22-(N-(7-nitrobenz-2-oxa-1,3-diazol-4-yl) amino)-23,24-bisnor-5-cholen-3B-yl linoleate (NBD-cholesteryl linoleate).

10. A non-radioactive method for measuring the activity of cholesteryl ester transfer protein, the method comprising the steps of:

adding a prepared sonicated particle to a buffer to form a buffered solution;

adding an emulsion of lipid to the buffered solution to accept the transfer of neutral lipid;

adding cholesteryl ester transfer protein to the buffered solution;

incubating the buffered solution; and reading the fluorescence of the buffer solution to measure the activity of the cholesteryl ester transfer protein.

11. The method according to claim 10, wherein the cholesteryl ester transfer protein is found in human plasma.

12. The method according to claim 10, wherein the buffer is 10 millimolars of trizma hydrochloride, 150 millimolars of sodium hydrochloride and 2 millimolars of ethylenediaminetetraacetic acid.

13. A non-radioactive method for measuring the activity of cholesteryl ester transfer protein comprising:

interacting cholesteryl ester transfer protein with a synthetic N-(7-nitrobenz-2-oxa-1,3-diazol-4-yl) amino (NBD-CE) emulsion said emulsion comprising donor particles;

shuttling NBD-CE molecules out of the emulsion; and releasing the NBD-CE from the cholesteryl ester transfer protein to an acceptor, wherein the acceptor is an emulsion comprising triglycerides and phosphatidylcholine.

14. The method according to claim 13, wherein the emulsion is a lipid emulsion of triglyceride and phosphatidylcholine.

15. The method according to claim 14, wherein the fluorescent intensity of the NBD-CE increases as the NBD-CE is moved from the synthetic HDL type emulsion to the acceptor.

16. A diagnostic kit for measuring the activity of cholesteryl ester transfer protein comprising:

a first glass vial having about 10 milliliters of a liquid mixture that includes:
125 microliters of a sonicated particle; and
about 9.875 milliliter of a buffer comprising 10 millimolars of trizma hydrochloride, 150 millimolars of sodium chloride and 2 millimolars of ethylenediaminetetraacetic acid, wherein the buffer has a pH between 7.0 and 8.0; and a second glass vial having a solution that includes:
50 microliters of an acceptor, wherein the acceptor is a lipid emulsion of triglyceride and phosphatidylcholine; and
9.5 milliliters of a buffer having 10 millimolars of trizma hydrochloride, 150 millimolars of sodium chloride and 2 millimolars of ethylenediaminetetraacetic acid, wherein the buffer has a pH between 7 and 8.

17. The diagnostic kit according to claim 16, further comprising a container for receipt of equal volumes of each vial.

18. The diagnostic kit according to claim 16, wherein first glass vial is an amber colored glass vial.

19. A method for making a synthetic donor particle for measuring the activity of cholesteryl ester transfer protein comprising:

sonicating at a predetermined sonication energy 2.8E-5 moles of N-(7-nitrobenz-2-oxa-1,3-diazol-4-yl) amino labeled neutral lipid with 13 mg of phosphatidylcholine to form an emulsion;

maintaining a temperature of 50 degrees centigrade for 45 minutes in a buffer 10 ml of 0.1M KCl/10 mM at a pH between 7 and 8.

lowering the temperature to 40 degrees centigrade and lowering the sonication energy to ⅔ of the predetermined sonication energy;

adding over a period of 15 minutes about 12 mg of an apolipoprotein apoA-I in 800 uL 2.5M urea; and centrifugalizing to remove titanium.

20. The method according to claim 19, wherein the predetermined sonication energy is a power output just under that which causes a sonic probe to cavitate within the emulsion.

21. A non-radioactive method for measuring the activity of cholesteryl ester transfer protein, the method comprising the steps of:

adding a prepared sonicated particle, said sonicated particle comprising at least an apolipoprotein, to a buffer to form a buffered solution;

adding an emulsion of lipid to the buffered solution to accept the transfer of a neutral lipid;

adding cholesteryl ester transfer protein to the buffered solution;

incubating the buffered solution; and, reading a fluorescence of the buffer solution to measure the activity of the cholesteryl ester transfer protein.

22. A non-radioactive method for measuring the activity of cholesteryl ester transfer protein comprising:

interacting cholesteryl ester transfer protein with a synthetic N-(7-nitrobenz-2-oxa-1,3-diazol-4-yl) amino (NBD-CE) emulsion, said emulsion comprising an apolipoprotein;

shuttling NBD-CE molecules out of the emulsion;

releasing the NBD-CE from the cholesteryl ester transfer protein to an acceptor, wherein the acceptor is an emulsion comprising triglycerides and phosphatidylcholine, and correlating said releasing with a measurement of the activity of said cholesteryl ester transfer protein.

23. A diagnostic kit containing reagents for measuring the activity of cholesteryl ester transfer protein, comprising:

a first container having a solution including sonicated particles, said sonicated particles each comprising an apolipoprotein, and a buffer having a pH between about 7.0 and about 8.0; and a second container having a solution including an acceptor, wherein the acceptor is a lipid emulsion of triglyceride and phosphatidylcholine, and a buffer a pH between about 7 and about 8;

whereby a combination of the reagents are sufficient to generate a fluorescence reading upon addition of a source of CEPT and sufficient incubation thereof.

24. A diagnostic kit containing reagents for measuring the activity of cholesteryl ester transfer protein, comprising:

a first container having a solution including sonicated particles, said sonicated particles each comprising an apolipoprotein, and a buffer comprising at least a compound containing hydrochloride, a salt, and an acid, wherein the buffer has a pH between 7.0 and 8.0; and a second container having a solution including an acceptor, wherein the acceptor is a lipid emulsion of triglyceride and phosphatidylcholine, and a buffer comprising at least a compound containing a hydrochloride, a salt and an acid, wherein the buffer has a pH between 7 and 8;

whereby a combination of the reagents are sufficient to generate a flourescence reading upon addition of a source of CEPT and sufficient incubation thereof.

25. A diagnostic kit containing reagents for measuring the activity of cholesteryl ester transfer protein, comprising:

a first container having a solution including sonicated particles, said sonicated particles each comprising an apolipoprotein, and a buffer, said buffer comprising trizma hydrochloride, sodium chloride and ethylenediaminetetraacetic acid, wherein the buffer has a pH between 7.0 and 8.0; and a second container having a solution including an acceptor, wherein the acceptor is a lipid emulsion of triglyceride and phosphatidylcholine, and a buffer, said buffer comprising trizma hydrochloride, sodium chloride and ethylenediaminetetraacetic acid, wherein the buffer has a pH between 7 and 8;

whereby a combination of the reagents are sufficient to generate a fluorescence reading upon addition of a source of CEPT and sufficient incubation thereof.

* * * * *